United States Patent [19]

Mitsuhashi et al.

[11] Patent Number: 4,812,444

[45] Date of Patent: Mar. 14, 1989

[54] DEHYDRATION OF HYDROUS MATTER USING ANHYDROUS GLYCOSYLFRUCTOSE

[75] Inventors: Masakazu Mitsuhashi; Shuzo Sakai; Toshio Miyake, all of Okayama, Japan

[73] Assignee: Kabushiki Kaisha Hayashibara Seibutsu Kagaku Kenkyujo, Okayama, Japan

[21] Appl. No.: 942,421

[22] Filed: Dec. 16, 1986

[30] Foreign Application Priority Data

Dec. 26, 1985 [JP] Japan ................. 60-292297

[51] Int. Cl.$^4$ .................. A61K 47/00; C08L 5/00
[52] U.S. Cl. ..................... 514/53; 514/777; 426/658; 536/102; 127/30; 127/38
[58] Field of Search ............ 514/53, 777; 536/102; 127/30, 38; 426/658

[56] References Cited

U.S. PATENT DOCUMENTS

| | | | |
|---|---|---|---|
| 3,865,957 | 2/1975 | Schieweck et al. | 426/658 |
| 3,973,050 | 8/1976 | Hayashibara et al. | 426/552 |
| 4,102,743 | 7/1978 | Yokobayashi et al. | 435/885 |
| 4,117,173 | 9/1978 | Schiweck et al. | 426/548 |
| 4,146,706 | 3/1979 | Hisatsuka et al. | 536/123 |
| 4,312,979 | 1/1982 | Takemoto et al. | 536/114 |
| 4,359,531 | 11/1982 | Bucke et al. | 426/536 |
| 4,386,158 | 5/1983 | Shimizu et al. | 435/178 |
| 4,556,429 | 12/1985 | Takazoe et al. | 426/658 |
| 4,572,916 | 2/1986 | Lindley et al. | 426/658 |
| 4,659,699 | 4/1987 | Francis | 536/124 |

FOREIGN PATENT DOCUMENTS

| | | |
|---|---|---|
| 448067 | 6/1936 | United Kingdom . |
| 551533 | 2/1943 | United Kingdom . |
| 1247249 | 9/1971 | United Kingdom . |
| 1293477 | 10/1972 | United Kingdom . |

*Primary Examiner*—Ronald W. Griffin
*Attorney, Agent, or Firm*—Browdy and Neimark

[57] ABSTRACT

A novel dehydration method using anhydrous glycosylfructose as the desiccant is disclosed. Anhydrous glycosylfructose is converted to the crystalline hydrate and acts as the desiccant when incorporated into a hydrous matter. Natural saccharides such as palatinose, raffinose, erlose, and melezitose can be used. The dehydration is applicable to hydrous matters, such as those of foods, pharmaceuticals, cosmetics, and their materials and intermediates.

8 Claims, No Drawings

DEHYDRATION OF HYDROUS MATTER USING ANHYDROUS GLYCOSYLFRUCTOSE

BACKGROUND OF THE INVENTION

1. Field of the Invention

The present invention relates to a method for dehydration of a hydrous matter.

More particularly, the present invention relates to a method for dehydrating a hydrous matter characterized by incorporating anhydrous glycosylfructose into the hydrous matter to convert the anhydrous glycosylfructose into crystalline glycosylfructose hydrate.

2. Definition

Throughout the specification, percentages and parts will be expressed by weight based on the dry solid, unless specified otherwise.

3. Description of the Invention

The moisture in foods greatly influences the physical properties and shelf lives. Generally, hydrous foods are susceptible to microbial contamination, as well as to alteration and deterioration such as hydrolysis, souring and browning.

As one method to decrease the moisture in the foods in order to prolong their shelf lives, various dehydration methods have been employed: for example, "sato-zuke (preservation in sugar)" as in the case of "buntan-zuke (a candied citrus fruit buntan)", "shio-zuke (pickling in salt)" as in the case of "takuan-zuke (a pickled Japanese radish)", and drying, as in the case of "funmat-su-miso (powdered soybean paste)" or "funmatsu-kaju (fruit juice powder)".

However, sugar has the disadvantages that its excessive sweetness does not suit the recent preference: that the intake of sugar is a major factor in causing dental caries and still that an excessive intake of sugar increases blood cholesterol. As to common salt, it has been pointed out that its excessive intake is one of the major causes of geriatric diseases such as hypertension and cancer. Thus, physicians advise patients to reduce salt intake as much as possible.

The drying method undesirably yields insipid foods because vaporization inevitably disperses flavor during the processing steps.

Pharmaceuticals containing a bioactive substance, for example, lymphokine, hormone, vitamin, intact bacteria cell or antibiotic, are produced generally by heat-drying or lyophilizing the bioactive substance along with a large amount of a stabilizer. This is because bioactive substances are unstable under high moisture conditions.

The stabilizers which have been used are watersoluble polymers such as albumin, casein, gelatin and hydroxylethyl starch.

Dehydration in the presence of these water-soluble polymers, however, has the disadvantage of consuming a relatively large amount of energy, insolubilizing the final product, and inactivating the bioactive substances.

SUMMARY OF THE INVENTION

In view of the foregoing, we have investigated the use of glycosylfructose in a desiccant which overcomes these drawbacks of conventional dehydration methods.

As the result, we found that anhydrous glycosylfructose, specifically, that containing a high-purity glycosylfructose with a glycosylfructose content of 90% or higher, act as a strong desiccant when incorporated into hydrous products, such as foods and pharmaceuticals, to effect conversion into crystalline glycosylfructose hydrate; and we found that tasty and high-quality dehydrated foods and stable and highlyactive pharmaceuticals can be easily prepared in this way.

DESCRIPTION OF THE PREFERRED EMBODIMENTS

The present invention utilizes anhydrous glycosylfrucotse which has drawn no attention as possible desiccant. The present invention is the first instance where a hydrous matter is dehydrated by incorporation of anhydrous glycosylfructose.

The dehydration method according to the invention is advantageous for dehydrating a matter which has a free moisture content but not of a binding water such as water of crystal, for example, to reduce the moisture in various hydrous matters, for example, those of foods, pharmaceuticals, cosmetics, chemicals, and their materials and intermediates.

We found that incorporation of anhydrous glycosylfructose strongly entraps about 5-20% of moisture from these hydrous products to substantially eliminate their moisture or even to bring them to dryness.

Furthermore, the practice of the present invention leads to no harm because glycosylfructose per se is a non-toxic and harmless natural sweetener. According to the invention, a high-quality food with a substantially-decreased moisture in the form of, for example, massecuite or powder, can be easily prepared by dehydrating a high-moisture content food in liquid or paste form, for example, brandy, fresh cream and mayonnaise. This method has the feature that such a high-moisture content food is easily converted into a tasty dehydrated form without undergoing alteration and deterioration because this method uses no vigorous processing step such as heat-drying.

We found that the inside space of a moistureproof package can be kept at highly-desiccated conditions first by adding anhydrous glycosylfructose in an amount exceeding the moisture in the hydrous food material to be enclosed therein to obtain a dehydrated food wherein the anhydrous glycosylfructose is partially converted into crystalline glycosylfructose hydrate, i.e. a dehydrated food containing both anhydrous glycosylfructose and crystalline glycosylfructose hydrate; then enclosing the dehydrated food in the moistureproof package so as to entrap the moisture in the package with the remaining anhydrous glycosylfructose. This decreases the relative humidity inside the moistureproof package.

Also it was found that, as a consequence of the dehydration process used, the present invention prevents alteration and deterioration such as microbial contamination, hydrolysis, souring or browning in dehydrated foods; and that the obtained tasty foods retain their high quality over a long period of time.

In the case of an aqueous solution of lymphokine or antibiotic, or a paste of a pharmaceutical product such as ginseng extract or snapping turtle extract, a high-quality pharmaceutical with a substantially-decreased moisture in, for example, massecuite or powder can be easily prepared by incorporating anhydrous glycosylfructose into the aqueous solution or paste to convert the anhydrous glycosylfructose into crystalline glycosylfructose hydrate.

This method provides a high-quality and stable pharmaceutical because the method requires no vigorous processing step such as heat-drying and also because anhydrous glycosylfructose acts as a stabilizer.

Conventional stabilizers such as water-soluble polymers can be suitably used to obtain a much more stabilized pharmaceutical without wasting energy for dehydration of the stabilizer.

The present invention can be advantageously practiced in the preparation of solid injection by, for example, placing a prescribed amount of anhydrous glycosylfructose in a vial; adding to the vial an aqueous solution containing a bioactive substance, for example, lymphokine or hormone, in an amount below the moisture that is required to convert completely the anhydrous glycosylfructose; and sealing the vial.

We found that, in such a case, anhydrous glycosylfructose dehumidifies the air inside the vial, as well as dehydrating the aqueous solution.

Also, it was found that, as a consequence of the drying method used, the present invention facilitates the preparation of dehydrated pharmaceuticals; and that the obtained pharmaceuticals retain their high quality over a long period of time and readily dissolve in water on use.

The anhydrous glycosylfructose usable in the invention is a substantially-anhydrous glycosylfructose which is convertible into crystalline hydrate to exhibit a strong dehydrating activity. The moisture content of such anhydrous glycosylfructose is generally lower than 3%, preferably, lower than 2%, as measured by the Karl Fischer's method. The glycosylfructose may be chosen among natural saccharides, for example, palatinose (or isomaltulose), lactulose, maltulose, raffinose, erlose, and melezitose. The saccharides may be commercially available, or may be prepared from a material containing glycosylfructose. More particularly, raffinose can be prepared prepared, for example, from soybean whey or beet syrup. Erlose can be prepared, as disclosed in Japan Patent Laid-Open No. 103,889/86, from a glucose-transferred product by cyclodextrin glucanotransferase. Melezitose can be prepared from Douglas fir sap.

The anhydrous glycosylfructose may be a commercialized anhydrous crystalline glycosylfructose powder, or an anhydrous glycosylfructose powder which is obtainable by heat-drying an aqueous glycosylfructose solution or crystalline glycosylfructose hydrate.

The present invention can be advantageously used when a high-quality dehydrated product in massecuite or powder form is prepared from a hydrous matter that is susceptive to alteration and/or deterioration during heat- or vacuum-drying.

The present invention is specifically advantageous when the hydrous products are those of origins such as animal, plant or microorganism, such as organ, tissue, cell, triturate, extract component, and preparations obtained therefrom.

In case the hydrous matter is a food, its material or intermediate in liquid or paste form, a stable and tasty dehydrated food can be easily prepared according to the invention. Examples of such hydrous matter are agricultural products such as fresh fruit, juice, vegetable extract, soybean milk, sesame paste, nut paste, "nama-an (unsweetened bean jam)", gelatinized starch paste and flour dough: marine products such as sea urchin paste, oyster paste and sardine paste; poultry or daily products such as fresh egg, lecithin, milk, whey, fresh cream, yogurt, butter and cheese; hydrous seasonings such as maple syrup, honey, "miso (soybean paste)", soy sauce, mayonnaise, dressing, bonito extract, meat extract, tangle extract, chicken extract, beef extract, yeast extract, mushroom extract, licorice extract, stevia extract, enzymatically processed product thereof and seasoning liquid for pickles; liquors such as Japanese sake, wine, brandy and whisky: soft drinks such as tea, green tea and coffee; hydrous spices such as those extracted from peppermint, "wasabi (Japanese horseradish)", garlic, mustard, "sansho (Japanese pepper tree)", cinnamon, sage, laurel, pepper, and citrus fruits; and hydrous coloring agents such as those extracted from madder, turmeric, paprika, red beet, safflower, cape jasmine, saffron, sorghum and Monascus microorganism.

The dehydrated products obtained in this way, for example, powdered agricultural- or poultry-product, powdered oil and fat, flavor powder and coloring agent powder, can be conveniently used, for example, as a natural bulk flavor excellent in taste and flavor, in various foods, for example, seasonings such as mayonnaise and soup stock; confectioneries such as hard candy and cake; and instant foods such as hot cake mix and instant juice.

In case the hydrous matter is a pharmaceutical, its material or intermediate, a stable and highly-active pharmaceutical can be easily prepared without losing or inactivating the effective ingredients. Examples of such hydrous matter are a solution containing lymphokine such as interferon, lymphotoxin, tumor necrosis factor, macrophage migration inhibitory factor, colony-stimulating factor, transfer factor or interleukin 2; a solution containing hormone such as insulin, growth hormone, prolactin, erythropoietin or follicle-stimulating hormone; a solution containing a biological such as BCG vaccine, Japanese encephalitis vaccine, tetanus toxoid, Trimeresurus antitoxin or human immunoglobulin; a solution containing antibiotic such as penicillin, erythromycin, chloramphenicol, tetracycline, streptomycin or kanamycin sulfate; a solution containing a vitamin such as thiamine, riboflavin, ascorbic acid, liver oil, carotenoid, ergosterol or tocopherol; a solution containing an enzyme such as lipase, elastase, urokinase, protease, $\beta$-amylase, isoamylase, glucanase or lactase; an extract such as ginseng extract, snapping turtle extract, chlorella extract or aloe extract; and cell paste such as that of lactic acid bacterium or yeast.

In case the hydrous matter is a cosmetic, its material or intermediate, a high-quality cosmetic can be easily prepared by dehydrating a hydrous matter such as fresh egg, lecithin, fresh cream, honey, licorice extract, flavor, coloring agent or enzyme similarly as in the case of foods or pharmaceuticals. The resultant product can be advantageously used as skin- and hair-treatments, and hair tonic.

In case the hydrous matter is an enzyme, the resultant product can be advantageously used in the catalyst for preparing foods, pharmaceuticals and chemicals, as well as in therapeutic, digestive and detergent compositions.

Anhydrous glycosylfructose is incorporated into a hydrous matter, for example, by mixing, kneading, dissolving, permeating, sprinkling, coating, spraying or injecting before the processing steps are over.

The amount of anhydrous glycosylfructose to be incorporated is, generally, in one part of a hydrous matter, 0.01–500 parts, desirably, 0.1–100 parts, but varies with the properties of the final product. To improve further the quality of the resultant product, one or more of flavor, coloring agent, seasoning, stabilizer and filler can be used along with anhydrous glycosylfructose.

Such stabilizer may be a water-soluble polymer that has been deemed difficulty dehydratable, and is not limited to a low-molecular weight compound such as conventional antioxidant because even such water-soluble polymer is strongly dehydrated with anhydrous glycosylfructose. For this reason, water-soluble polymers, for example, soluble starch, dextrin, cyclodextrin, pullulan, elsinan, dextran, xanthan gum, gum arabic, locust bean gum, guar gum, tragacanth gum, tamarind gum, carboxymethyl cellulose, hydroxyethyl cellulose, hydroxyethyl starch, pectin, agar, gelatin, albumin and casein, can be advantageously used as the stabilizer.

When such water-soluble polymer is used, a dehydrated food with microcrystals of glycosylfructose hydrate can be prepared first by homogenously dissolving a water-soluble polymer in a hydrous product in, for example, liquid or paste form; then incorporating anhydrous glycosylfructose homogenously into the resultant solution with a suitable procedure such as mixing or kneading. In the resultant food, the flavor- and effective-components are coated with a membrane of the water-soluble polymer, or enclosed together with the glycosylfructose hydrate microcrystals in a microcapsule of the membrane. When cyclodextrin is used in combination with anhydrous glycosylfructose, a possible dispersion, alteration and/or deterioration of the above described components is prevented by formation of inclusion complexes. For this reason, this method superiorly retains the flavor- and effective-components that are present in hydrous matters.

In the present invention, various procedures can be used for preparing dehydrated products, specifically, those in pulverulent form. For example, anhydrous glycosylfructose is incorporated homogenously into a hydrous matter, such as food, pharmaceutical, chemical, material or intermediate therof, with a relatively high moisture to give a moisture content of about 40% or lower, desirably, about 10–30%, and the resultant mixture is allowed to stand at a temperature of about 10°–50° C., for example, ambient temperature, for about 1–10 days to convert the anhydrous glycosylfructose into crystalline glycosylfructose hydrate to obtain a block which is then pulverized by scraping, cutting or crushing. If necessary, drying- and sieving-steps may follow the pulverization.

The spraying method directly provides such powder. For example, a prescribed amount of a hydrous matter in liquid or paste form is sprayed towards a fluidizing anhydrous glycosylfructose to effect granulation, and then aged at about 30°–60° C. for about 1–24 hours to convert the anhydrous glycosylfructose into crystalline glycosylfructose hydrate. Alternatively, a powder obtained by mixing or kneading anhydrous glycosylfructose with a hydrous matter in liquid or paste, and, immediately or after starting the conversion, spraying the resultant mixture is aged similarly. These methods are favorable for preparing a pulverulent product on a large scale.

The spraying method can be advantageously practiced by using a minimum amount of crystalline glycosylfructose hydrate to accelerate the conversion and to shorten the subsequent ageing.

The powder obtained in this way can be shaped, prior to its use, into any form, for example, granule, tablet, capsule, rod, plate or cube, alone or, if necessary, in combination with filler, vehicle, binder and/or stabilizer, prior to its use.

Generally, starch requires a relatively large amount of moisture in its swelling and gelatinization. For this reason, gelatinized starch is susceptive to microbial contamination. Anhydrous glycosylfructose can be advantageously used to dehydrate gelatinized starch. For example, microbial contamination of a gelatinized starch product such as "gyuhi (a rice paste)" can be prevented by incorporating anhydrous glycosylfructose to convert it into crystalline glycosylfructose hydrate and to decrease the moisture in the product.

Furthermore, incorporation of anhydrous glycosylfructose extremely prolongs the shelf lives of processed foods that contain gelatinized starch because anhydrous glycosylfructose disperses homogenously in the gelatinized starch and acts as an agent that prevents retrogradation.

Anhydrous glycosylfructose exhibits a high affinity to alcohols. Because of this property, anhydrous glycosylfructose can be advantageously used as the desiccant for alcohols and alcohol-soluble matters, such as methanol, ethanol, butanol, propylene glycol and polyethylene glycol. For example, a dehydrated liquor in massecuite or powder can be prepared by dehydrating a liquor such as Japanese sake, "shochu (a Japanese distilled spirits)", wine, brandy, whisky or vodka: their effective component and flavor being retained in the resultant crystalline glycosylfructose. The obtained liquor powder can be used in confectioneries and premixes, as well as in beverages after dissolution in water.

In the above case, anhydrous glycosylfructose imparts a mild sweetness, body and appropriate viscosity to the liquor, as well as dehydrating and stabilizingtthe liquor.

The present invention can be advantageously practiced in the preparation of ointments in massecuite form with an appropriate viscosity, spreading rate and adhesiveness that stably retain their effective element such as iodine by mixing an alcoholic solution of iodine with anhydrous glycosylfructose, and adding an aqueous solution containing a water-soluble polymer to the resultant mixture to convert the anhydrous glycosylfructose into crystalline glycosylfructose hydrate.

Anhydrous glycosylfructose exhibits an unexpectedly high affinity to oil and fat though it is a hydrophilic saccharide.

Because of this property, anhydrous glycosylfructose can be advantageously used as the desiccant for oil-soluble substance, emulsion or latex, specifically, as the desiccant that entraps the trace moisture in oil-soluble substances. Examples of such oil-soluble substances are fats and oils such as soybean oil, rapeseed oil, mustard oil, sesame oil, safflower oil, palm oil, cacao butter, beef tallow, lard, chicken oil, marine oil and hardened oil; oil-soluble spices such as citrus essential oil, flower essential oil, spice oil, peppermint oil, spearmint oil, cola nut extract and coffee extract; oil-soluble coloring agent such as beta-carotin, paprika pigment, annotto pigment and chlorophyll; oil-soluble vitamins such as liver oil, vitamin A, vitamin $B_2$ lactate, vitamin E, vitamin K and vitamin D; oil-soluble hormones such as estrogen, progesterone and androgen; and unsaturated higher fatty acids such as linoleic acid, linolenic acid, arachidonic acid, eicosapentaenoic acid and docosahexaenoic acid.

The resultant dehydrated oil-soluble substances are characterized by their high-quality and low susceptivity to alteration and deterioration such as by hydrolysis and souring.

This method can be advantageously practiced in the preparation of pulverulent foods such as those of oil and fat, spice, flavor and coloring agent, pulverulent cosmetics, and pulverulent pharmaceuticals such as those of vitamin and hormone by impregnating or mixing an oil-soluble substance in anhydrous glycosylfructose.

In this case, anhydrous glycosylfructose acts as the desiccant, as well as a stabilizer, retainer, vehicle and carrier.

As described above, the present invention is based on the finding that anhydrous glycosylfructose strongly dehydrates various hydrous products. By using anhydrous glycosylfructose as the desiccant, foods, cosmetics and pharmaceuticals that have a decreased moisture and high-quality can be prepared from a hydrous product in liquid or paste form without causing deterioration and/or dispersion of taste and flavor in foods and cosmetics, and decomposition and/or inactivation of their effective components in pharmaceuticals.

In addition to the above mentioned special uses, anhydrous glycosylfructose can be advantageously used in the preparation of foods, pharmaceuticals and cosmetics because anhydrous glycosylfructose is a natural sweetener and has the inherent feature of glycosylfructose that it imparts a mild sweetness, body, texture, viscosity and moisture-retaining properties to these matters without fear of increasing their cariogenicty and blood cholesterol.

Several embodiments and superior effects of the present invention will be hereinafter described.

EXAMPLE 1

"Oboro-fu Gyuhi"

Four kilograms of waxy rice powder was dissolved in 6,000 ml of water, and the resultant was poured into a wet cloth extended over a wooden frame and steamed at 100° C. for 20 minutes. The resultant product was kneaded together with 8 kg of a commercialized anhydrous crystalline glucose powder and 1 kg of sucrose, added with 1 kg of corn syrup, sufficiently kneaded, shaped and allowed to stand under ambient conditions for 16 hours to convert the anhydrous glucose into crystalline glucose hydrate at the outer layer of the resultant product. Thereafter, the product was subjected briefly to roll crusher to crack the surface.

The product was excellent in taste and flavor and scarcely susceptive to microbial contamination, and retained its high-quality over a long period of time.

EXAMPLE 2

Fondant Containing Mayonnaise

Five kilograms of mayonnaise was admixed with 5 kg of an anhydrous erlose powder to convert it into crystalline erlose hydrate.

The product can be advantageously used in confectioneries.

The chilled product with a mayonnaise flavor is suitable for frozen dessert.

EXAMPLE 3

French Dressing Powder

Two kilograms of French dressing was mixed with 8 kg of an anhydrous raffinose powder, transferred into a tray, and blocked by 2-day standing to convert the anhydrous raffinose into crystalline raffinose hydrate.

The block was then pulverized with a scraper and sieved to obtain a French dressing powder excellent in taste and flavor.

The product can be advantageously used for sprinkling on vegetable salad, as well as for seasoning fresh vegetables for sandwich.

EXAMPLE4

Brandy Powder

Ten g of pullulan was dissolved in 2,000 ml of brandy, and the resultant solution was mixed with 8 kg of an anhydrous raffinose powder, blocked and pulverized similarly as in Example 3 to obtained a brandy powder.

The product is a powder flavor that exhibits in the mouth an appropriate sweetness and a satisfactory brandy flavor.

The product can be advantageously used for flavoring tea, as well as preparing confectioneries such as premixes and candies.

The product can be advantageously shaped with granulator or tabletting machine, prior to its use.

EXAMPLE 5

Powdered "Miso"

One kilogram of "aka-miso (a reddish soybean paste)" was mixed with 3 kg of an anhydrous palatinose powder, poured into wells provided on a metal plate, solidified by allowing at ambient temperature overnight and removed from the wells to obtain "miso" solids, about 4 g each, which were then subjected to a pulverizer to obtain a "miso" powder.

The product can be advantageously used as the seasoning for instant Chinese noodle and instant "miso" soup.

Additionally, the product is usable in confectioneries.

EXAMPLE 6

Soy Sauce Powder

One part of "usukuchi-shoyu (a soy sauce with a relatively thin taste)" was sprayed onto 4 parts of an anhydrous erlose powder and 0.02 parts of crystalline erlose hydrate both fluidizing on a conveyer, after which the resultant product was conveyed outside towards an ageing tower and allowed to stand in the tower at 30° C. overnight to convert the anhydrous erlose into crystalline erlose hydrate.

The product can be advantageously used as the seasoning for instant Chinese noodle and instant soup.

Example 7

Yolk Powder

A yolk prepared with fresh eggs was pasteurized at 60°–64° C. with a plate-type heat-pasteurizer, and one part of the obtained yolk fluid was added with 3.5 parts of an anhydrous raffinose powder, blocked and pulverized similarly as in Example 3 to obtain a yolk powder.

The product can be advantageously used in premixes, frozen desserts and emulsifiers, as well as in baby food and nutritious diet such as liquid food for peroral- or parenteral-administration.

Additionally, the product can be advantageously used in skin treatment and hair tonic.

EXAMPLE 8

Powdered Butter

Ten kilograms of butter was mixed with 20 kg of an anhydrous melezitose powder with a mixer, blocked and pulverized similarly as in Example 3 to obtain a butter powder.

The product can be advantageously used in premix, potage soup, stew and "chahan (a Chinese fried rice)", as well as in a nutritious diet such as intubation feeding.

EXAMPLE 9

Cream Powder

Two kilograms of fresh cream was mixed with 7 kg of an anhydrous palatinose powder, blocked and pulverized similarly as in Example 3 to obtain a cream powder.

The cream powder, which is excellent in taste and flavor, can be advantageously used for seasoning coffee and tea, as well as preparing premix, frozen dessert, cake, candy and a nutritious diet such as intubation feeding.

Also, the product can be advantageously used in skin treatment and as a hair tonic.

EXAMPLE 10

Yogurt Powder

Two kg of plain yogurt was mixed with 10 kg of an anhydrous erlose powder, blocked and pulverized similarly as in Example 3 to obtain a yogurt powder.

The product is excellent in taste and flavor, and stably retains the lactic acid bacteria over a long period of time. The product can be advantageously use to prepare premix, frozen dessert and cake, as well as to prepare nutritious diet such as intubation feeding.

The biochemicals obtained by shaping the product with granulator or tabletting machine can be advantageously used as the medicine for intestinal disorders.

EXAMPLE 11

Hot Cake Mix

Two hundred grams of flour was mixed with 60 g of a yolk powder obtained by the method in Example 7, 78 g of a butter powder obtained by the method in Example 8, 10 g of sucrose, 12 g of baking powder and 0.5 g of salt to obtain a hot cake mix.

A tasty hot cake can be easily prepared by dissolving the product in water or milk, and baking the resultant mixture.

EXAMPLE 12

Ginseng Extract Powder

Five hundred grams of ginseng extract was kneaded with 1.5 kg of an anhydrous melezitose powder, blocked and pulverized similarly as in Example 3.

The resultant powder was then fed to a granulator together with appropriate amounts of vitamin $B_1$ and vitamin $B_2$ powders to obtain a ginseng granule containing vitamins.

The product can be advantageously used as a tonic, hair treatment and medicine for relieving fatigue.

EXAMPLE 13

Solid Composition for Fluid Food

Twenty-five gram aliquots of a composition consisting of 500 part of an anhydrous raffinose powder, 270 parts of a yolk powder obtained by the method in Example 7, 209 parts of defatted milk, 4.4 parts of sodium chloride, 1.85 parts of potassium chloride, 4 parts of magnesium sulfate, 0.01 part of thiamine, 0.1 part of sodium ascorbate, 0.6 parts of vitamin E acetate, and 0.04 parts of nicotinamide were packed in small moistureproof laminated bags, followed by heat-sealing.

The composition decreases the moisture in the bag and requires no low-temperature storage because it is stable over a long period of time even at ambient temperature.

The product is excellently dispersible and soluble in water.

One pack of the product, dissolved in about 150-300 ml of water, can be used as the liquid food in peroral- or parenteral-administration through the nasal cavity, stomach or intestine.

EXAMPLE 14

Solid Injection

Newborn hamsters were injected with antiserum prepared in conventional manner to weaken their immunoreaction, implanted subcutaneously with BALL-1 cell and fed in usual manner for 3 weeks. The tumor masses, formed subcutaneously in the body of the hamsters, were extracted, minced and disaggregated in saline. The cell thus obtained was washed with serum-free RPMI 1640 medium (pH 7.2), suspended in a fresh preparation of the same culture medium to give a cell density of about $2 \times 10^6$ cells/ml, and incubated at 35° C. The culture medium was added with 200 U/ml of a partially-purified human interferon, incubated at this temperature for an additional 2 hours, added with about 300 hemagglutination titer/ml of Sendai virus, and incubated for an additional 20 hours to induce human interferon production. The resultant culture was then centrifuged at about $1,000 \times g$ and 4° C. to remove the sediment, and the supernatant was filtered with a membrane filter. The filtrate was passed through a column of immobilized anti-interferon antibody in conventional manner, and the non-adsorbed part was removed. The adsorbed part was then eluted and concentrated with a membrane to obtain a liquid preparation, concentration of about 0.01 w/v %, specific activity of about $1.5 \times 10^8$ U/mg protein, in the yield of about 4 ml per hamster.

Eight gram aliquots of a pyrogen-free anhydrous raffinose were placed in 100 ml moistureproof plastic bottles which were then added with 0.2 ml aliquot of the interferon concentrate (about $3 \times 10^6$ U), rubber-stopped and cap-sealed sterilely to obtain a solid injection.

This process has the advantages that it requires no treatment, apparatus and energy for lyophilization because the interferon-containing solution is dehydrated only by adding dropwisely it to a portion of anhydrous raffinose powder, as well as that it effectively stabilizes interferon.

Since the product is readily dissolvable in water, it can be advantageously used as the test reagent, antiviral agent or antioncotic for subcutaneous, intramascular or intravenous injection.

The titer of human interferon was assayed by the conventional plaque reduction method, and the hemagglutination titer was measured by the method as reported by J. E. Salk, The Journal of Immunology, Vol. 49, pp. 87-98 (1944).

EXAMPLE 15

Solid Injection

Newborn hamsters were injected with an antiserum prepared from rabbit in conventional manner to weaken their immunoreaction, implanted subcutaneously with an established SV-40 virus-transformed human monocyte, fed in usual manner for one week, injected intraperitoneally with $10^7$ viable BCG cells and fed for an additional 2 weeks. The tumor masses, formed subcutaneously in the body of the hamsters, about 15 g each, were extracted, minced and disaggregated by suspending in saline containing trypsin. The obtained cell was washed with Eagle's minimal essential medium (pH 7.2), supplemented with 5 v/v % human serum, diluted with a fresh preparation of the same culture medium, prewarmed to 37° C., to give a cell density of about $5 \times 10^6$ cells/ml, added with about 10 μg/ml of *E. coli* endotoxin, and incubated at this temperature for 16 hours to induce tumor necrosis factor production.

The resultant culture was then centrifuged at about $1,000 \times$ g and 4° C. to remove the sediment, and the supernatant was dialyzed against saline containing 0.01 M phosphate buffer (pH 7.2) for 21 hours, filtered with a membrane filter, concentrated and lyophilized to obtain a powder possessing tumor necrosis factor activity. The obtained powder was then purified with adsorption and descrption using ion exchange, molecular weight fractionation using gel filtration, concentration and filtration using membrane filter in accordance with the method as reported in G. Bodo, *Symposium on Preparation, Standardization and Clinical Use of Interferon*, 11th International Immunobiological Symposium 8 & 9, June 1977, Zagreb, Yugoslavia, to remove the interferon, and the resultant interferon-free product was purified by salting-out using ammonium sulfate and affinity-chromatography using concanavalin A-bound Sepharose to obtain an about 0.01 w/v % concentrate containing tumor necrosis factor in the yield of about 30 ml per hamster. Tumor necrosis factor is characterized in that it affects hemorrhagic cytolysis on Meth A sarcoma but no affects on normal human cells. The tumor necrosis factor obtained in this way was a glycoprotein with a specific activity of about $3.5 \times 10^5$ U/mg protein and free of the inducer used.

Fifty gram aliquots of a pyrogen-free anhydrous erlose were placed in 600 ml glass bottles, added with 0.5 ml of the concentrate containing tumor necrosis factor (about $1.75 \times 10^3$ U), rubber-stopped and cap-sealed under sterilely to obtain a solid injection.

This process has the advantages that it requires no treatment, equipment and energy for lyophilization because the solution containing tumor necrosis factor is dehydrated by anhydrous erlose powder, as well as that it effectively stabilizes tumor necrosis factor.

Since the product is readily dissolvable in water, it can be advantageously used as the antioncotic, hyperalimentation and injection for instillation.

The titer of tumor necrosis factor was assayed by the method in *Lymphokines*, Vol. 2, pp. 235–272 "Tumor Necrosis Factor" (1981), wherein L-929 cell that is sensitive to tumor necrosis factor is cultured for a prescribed time, followed by counting of the number of the viable cells.

EXAMPLE 16

Ointment for Treating Trauma

Three grams of iodine in 50 ml methanol was admixed with 500 g of an anhydrous erlose powder, mixed with 200 ml of 10 w/v % aqueous pullulan solution, and allowed to stand at ambient temperature overnight to convert the anhydrous erlose into crystalline erlose hydrate to obtain an ointment with appropriate spreading rat and adhesiveness.

The product can be used for treating trauma such as incised wound, abrasion, burn and trichophytic ulcer by applying it directly onto the trauma surface, or by applying it on gauze or oilpaper which is then placed on the trauma surface.

The deinfectant- and alimentary-activities of the erlose in the product shortens the healing period and heals trauma well.

As is apparent from the above, the present invention relates to a dehydration method wherein a hydrous matter is dehydrated by incorporating into it an anhydrous glycosylfructose to convert it into crystalline glycosylfructose hydrate. The present invention can be advantageously used to decrease the moisture content of various hydrous matters, for example, foods, pharmaceuticals, cosmetics, chemicals, and their materials and intermediates.

Since, in the present invention, a substantial dehydration is effected by converting an anhydrous glycosylfructose into crystalline glycosylfructose hydrate, therefore, vigorous processing conditions conditions such as heat-drying are not required, a high-quality dehydrated products can be prepared without deteriorating hydrous matters, for example, foods which tend to lose their flavor, and pharmaceuticals which tend to decompose or inactivate their effective ingredient.

The dehydrated products obtained in this way retain their high-quality over a long period of time because alteration and deterioration such as microbial contamination, hydrolysis, souring and browning are prevented in the product.

While a preferred embodiment of the invention has been described using specific terms, such description is for illustrative purpose only, and it is to be understood that changes and variations may be made without departing from the spirit or scope of the following claims.

We claim:

1. A method for dehydrating a hydrous product, comprising incorporating an anhydrous glycosylfructose into the hydrous product to convert said anhydrous glycosylfructose into crystalline glycosylfructose hydrate.

2. The method of claim 1, wherein said anhydrous glycosylfructose is a high-purity glycosylfructose having a glycosylfructose content of 90% or higher, based on the dry solid.

3. The method of claim 1, wherein said anhydrous glycosylfructose is in pulverulent form.

4. The method of claim 1, wherein the moisture content of said anhydrous glycosylfructose is lower than 3 w/w %.

5. The method of claim 1, wherein 0.01 to 500 parts by weight of an anhydrous glycosylfructose is incorporated into one part by weight of a hydrous product.

6. The method of claim 1, wherein the glycosylfructose is a member selected from the group consisting of palatinose, raffinose, erlose, melezitose, and mixtures thereof.

7. The method of claim 1, wherein said hydrous product is a member selected from the group consisting of food products, pharmaceuticals, cosmetics, and materials and intermediates thereof.

8. The method of claim 1, wherein said hydrous product contains a member selected from the group consisting of gelatinized starch, alcohol, oil-soluble substance and bioactive substance.

* * * * *